United States Patent [19]

Nishimura et al.

[11] Patent Number: 5,478,926
[45] Date of Patent: Dec. 26, 1995

[54] MONOCLONAL ANTIBODY AGAINST HUMAN IGE

[75] Inventors: Shinji Nishimura; Shigenori Harada, both of Osaka, Japan

[73] Assignee: Shionogi & Co., Ltd., Osaka, Japan

[21] Appl. No.: 145,317

[22] Filed: Nov. 3, 1993

Related U.S. Application Data

[63] Continuation of Ser. No. 686,405, Apr. 17, 1991, abandoned.

[30] Foreign Application Priority Data

Sep. 18, 1990 [JP] Japan ..................... 2-249530

[51] Int. Cl.$^6$ .................... C07K 16/42; C07K 16/18; G01N 33/53; G01N 33/577
[52] U.S. Cl. .................... 530/388.25; 530/388.73; 530/389.3; 530/389.6; 530/862; 435/7.1; 436/513; 436/536; 436/540; 436/548; 424/145.1; 424/153.1; 424/158.1; 424/172.1
[58] Field of Search ............. 435/70.21, 240.27, 435/7.1, 971; 530/388.25, 388.73, 388.9, 389.3, 389.6, 389.8, 862; 436/513, 536, 540, 548; 424/145.1, 158.1, 153.1, 173.1

[56] References Cited

FOREIGN PATENT DOCUMENTS 0259585  3/1988  European Pat. Off..
2585837  6/1987  France .

OTHER PUBLICATIONS

Nakamura et al., "Chapter 27" frm Handbook of Exp Immunol, vol. 1: Immunochemistry, Ed. D. M. Weir, Blackwell Sci Pub., 1986, pp. 27.1–27.20.
Anfosso et al, Conformational Differences of Human IgE on Hydrophobic and Hydrophilic Solid Phases Detected by Monoclonal Antibodies, Molec. Immunol., Nov. 1987, 24(11) pp. 1129–1134.
Chretien et al, A Monoclonal Anti–IgE Antibody Against an Epitope in the $CH_3$ Domain Inhibits IgE Binding to the Low Affinity IgE Receptor, J. Immunol., Nov. 1988, 141(a) pp. 3128–3134.
Kornfeld et al, Interaction of Immunoglobulin Glycopeptides with Concanavalin A, J. Biol. Chem., Apr. 1975, 250(7), pp. 2614–2619.
Patent Abstracts of Japan, vol. 12, No. 398, p. 6 C 538 (1988).
Grassi et al, J. Allergy Clin. Immunol., vol. 77, No. 6, pp. 808–822 (1986).
Ichimori et al, Hybridoma, vol. 4, No. 1, pp. 47–53 (1985).

Primary Examiner—Margaret Parr
Assistant Examiner—Ron Schwadron
Attorney, Agent, or Firm—Birch, Stewart, Kolasch & Birch

[57] ABSTRACT

The present invention provides novel monoclonal antibodies HE-22A, HE-35A, HE-39E, and HE-69B against human IgE, a mixture thereof, hybridomas producing the antibodies, and immunoassays of human IgE employing the antibodies, which are useful for clinical diagnosis of allergic diseases or parasitic infections.

1 Claim, 3 Drawing Sheets

● : Intact IgE
○ : Heat-Treated IgE

Immobilized Antibody: Indicated by underline

Labelled Antibody: ●:HE-22A, ■:HE-35A, ▲:HE-39E, ▼:HE-69B

MONOCLONAL ANTIBODY AGAINST HUMAN IGE

This application is a continuation, of application Ser. No. 07/686,405 filed on Apr. 17, 1991, now abandoned.

FIELD OF THE INVENTION

The present invention relates to monoclonal antibodies against human immunoglobulin E (IgE), a mixture thereof, hybridomas producing the monoclonal antibodies, and immunoassays of human IgE employing the monoclonal antibodies. The monoclonal antibodies according to the present invention are useful for clinical diagnostic agents to determine human IgE.

Prior Art

IgE is an immunoglobulin identified in 1966 by Ishizaka et al and it binds to mast cell or basophil surface via Fc receptor and reacts with allergens, thereby causing an immediate-type allergy. An IgE level in blood is quite low as compared with other immunoglobulins, but it significantly increases in the cases of allergic diseases, hepatic failure and parasitic infections, thus being characterized by the broad range of the levels in blood. Accordingly, to determine IgE level in blood is useful for diagnosis of allergic diseases or parasitic infections. The methods commonly used for this purpose include radioimmunoassay (RIA) and enzyme immunoassay (EIA) methods.

Monoclonal antibodies specifically reacting with human IgE have already been reported by Ichimori et al (Hybridoma, 4, 47 (1985)) and a method for determining human IgE in blood employing human IgE-specific monoclonal antibodies has also been reported by J. Grassi et al (J. Allergy. Clin. Immunol., 77, 808 (1986)). However, when such a conventional method employing monoclonal antibodies is used to determine human blood IgE, problems such as limited range of the determination and complicated determination procedure are experienced. Further, since the calibration curve is not always linear, the sensitivity is varied depending on the range of the concentrations to be determined and all the concentrations so determined are not reliable. The conventional methods also require special devices. All these problems and inconvenience can not be eliminated at a stretch by the conventional methods.

SUMMARY

Human IgE-specific monoclonal antibodies HE-22A, HE-35A, HE- 39E, and HE-69B provided by the present invention are characterized in that any one of the four monoclonal antibodies binds to human IgE at the region different from those the other three bind to without the one receiving any interference from the other three antibodies. Further, the 4 monoclonal antibodies bind to human IgE with different affinities so that the reactivity of a mixture of the antibodies with the human IgE can be controlled by appropriately mixing them. Based upon these properties, the human IgE-specific antibodies of the present invention can be used to determine quite easily human IgE levels of a wide range in blood with higher reliability without using any special devices. Accordingly, the monoclonal antibodies of the present invention can routinely be used as clinical diagnostic agents to determine human IgE.

DETAILED DESCRIPTION OF THE INVENTION

Figure 1A:
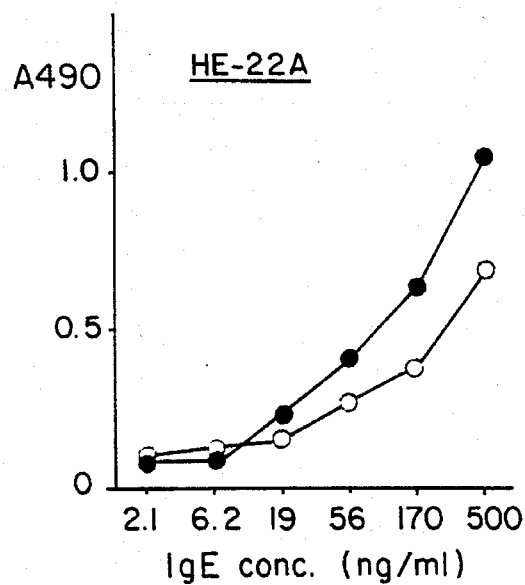
FIG. 1 shows the reactivity of each monoclonal antibody according to the present invention with heat-treated IgE.
Figure 1B:
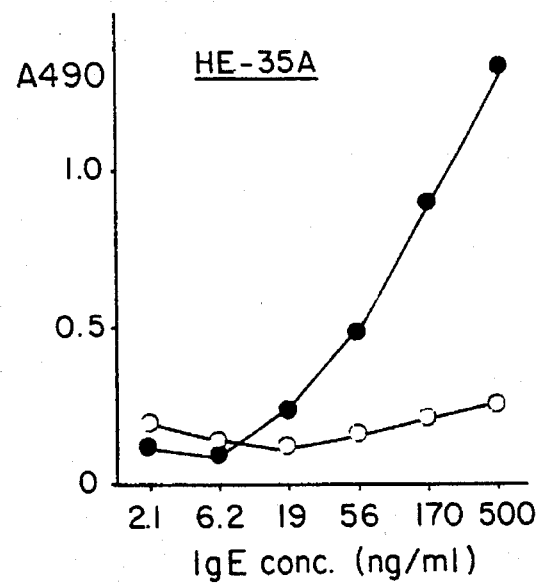
Figure 1C:
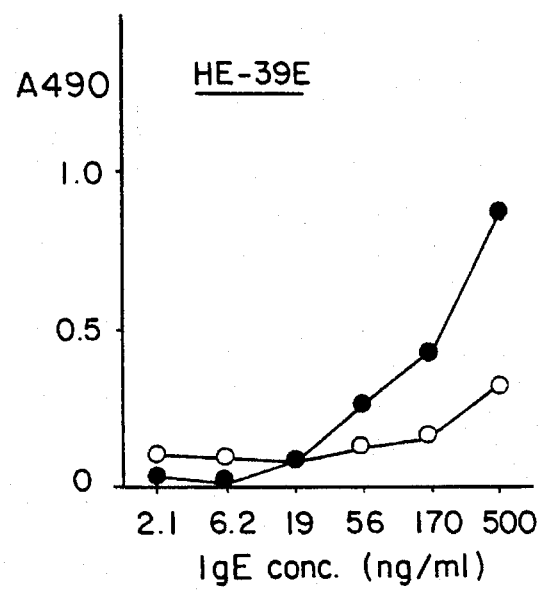
Figure 1D:
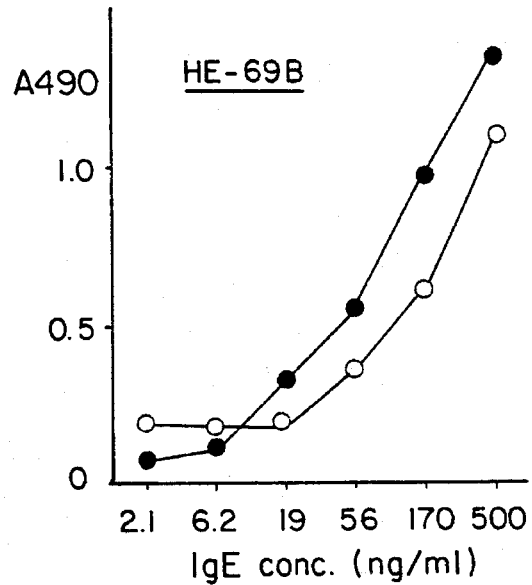
Figure 2A:
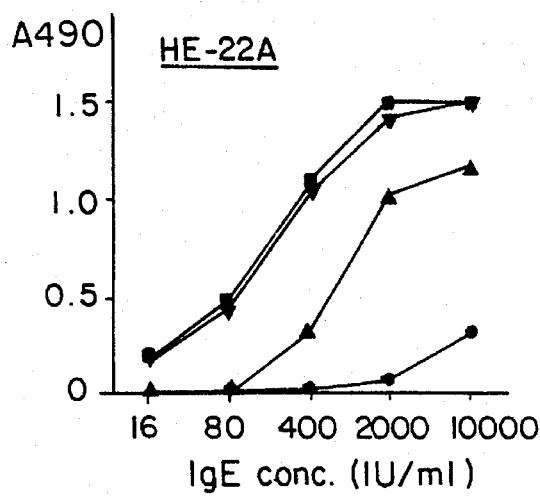
FIG. 2 shows sensitivity curves for IgE in sandwich ELISA system using combinations of the present monoclonal antibodies.
Figure 2B:
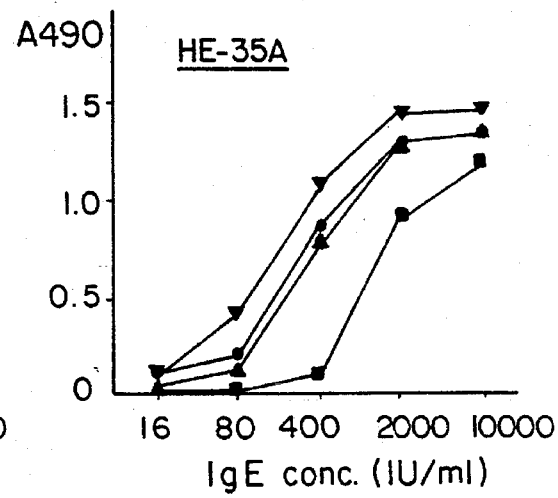
Figure 2C:
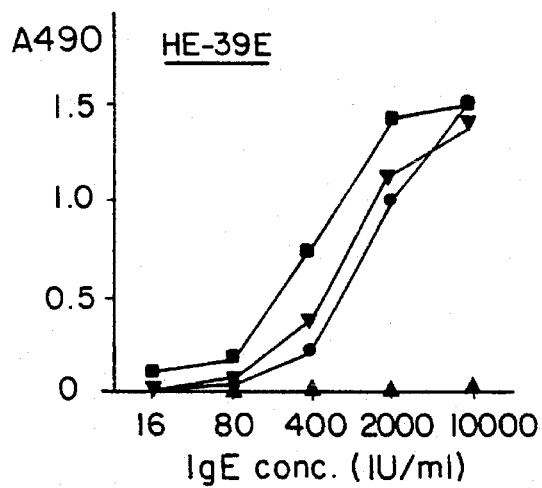
Figure 2D:
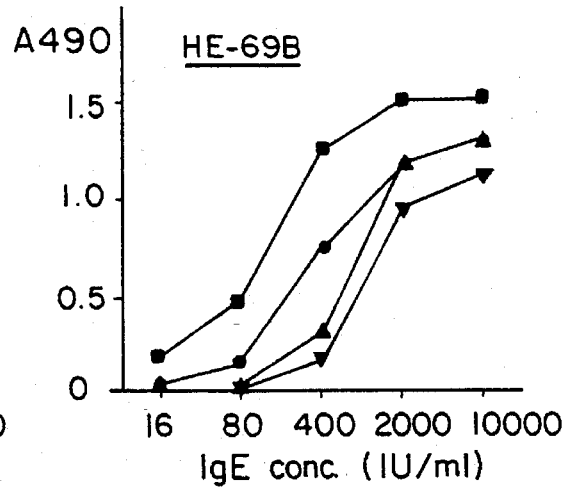

Human IgE-specific monoclonal antibodies provided by the present invention are characterized in that any one of the four monoclonal antibodies binds to human IgE at the region different from those the other three bind to without the one receiving any interference from the other three of the antibodies. In addition, the 4 human IgE-specific monoclonal antibodies bind to human IgE with different! affinities so that the reactivity of a mixture of the antibodies to the human IgE can be controlled by appropriately mixing them. Based on these properties, human IgE-specific antibodies according to the present invention can be used to determine quite easily a wide range of human IgE levels in blood with a higher reliability without using any special devices. Accordingly, the monoclonal antibodies of the present invention can routinely be used as clinical diagnostic agents to determine human IgE.

1) Preparation of hybridoma

Mice are immunized with human IgE. Cells capable of producing antibodies are obtained from the immunized mice and fused with myeloma cells, and resulting hybridoma cells are screened for the production of antibodies which react highly with the immunogen human IgE and differently derived human IgE but not with human IgG. Hybridomas selected are cloned and examined intensively for the reaction specificity of the produced antibody with 3 differently derived human IgEs, human IgA, human IgM, and human IgG, and clones producing antibodies which react highly with the immunogen human IgE and differently derived human IgEs but not with other human immunoglobulins are selected and incubated to yield monoclonal antibodies. The procedures of immunization, cell fusion, and screening of fused cells can be conducted by standard methods.

2) Preparation of monoclonal antibodies

Selected hybridomas are proliferated by in vitro or in vivo incubation to obtain monoclonal antibodies. In the case of in vitro incubation, hybridomas are incubated in complete RPMI medium until the proliferation limit is achieved and then the supernatant of the medium is recovered, from which monoclonal antibodies are obtained. In the case of in vivo incubation, BALB/c mice previously administered with pristane intraperitoneally are transplanted with $5 \times 10^6 - 10^7$ hybridoma cells intraperitoneally and about 3 weeks after the transplantation the mice are observed to ensure the swelling of the abdomens and ascitic fluid is taken, from which IgG fraction is isolated to obtain monoclonal antibodies.

In the present invention, according to the method mentioned above were obtained the monoclonal antibodies HE-39E, HE-22A, HE-69B, and HE-35A which specifically bind to human IgE. Hybridomas HE-39E Shionogi, HE-22A Shionogi, HE-69B Shionogi, and HE-35A Shionogi, which produce these antibodies, have been deposited with the Fermentation Research Institute (1–3, Higashi 1 chome, Tsukuba-Shi, Ibaraki-Ken, Japan) since Feb. 27, 1990 under the accession Nos. FERM P-11381, FERM P-11382, FERM P-11383 and FERM P-11384, respectively, and have been deposited with the same under the terms of Budapest Treaty since Apr. 4, 1991 with the accession Nos. FERM BP-3342, FERM BP-3343, FERM BP-3344 and FERM BP-3345, respectively.

The monoclonal antibodies according to the present invention do not react with any of human IgA, IgG, and IgM, while they react highly with human IgE. $\lambda$ and human IgE.$\kappa$, that is, specifically to human IgE.

Monoclonal antibody HE-22A did not react with human IgE which have been treated with endoglycosidase F capable of cleaving sugar chains of glycoproteins, thereby being deduced to recognize the structure closely related to sugar chains of human IgE.

Monoclonal antibody HE-35A has significantly low reactivity to heat-modified human IgE and, therefore, recognizes D$\epsilon$2 domain of human IgE since the structure of D$\epsilon$2 domain of human IgE is modified by heating.

Monoclonal antibodies HE-39E and HE-69B recognize D$\epsilon$1 domain of human IgE since their binding to human IgE was inhibited by commercially available monoclonal anti D$\epsilon$1 antibody (Serotech). However, each one of monoclonal antibodies HE-39E and HE-69B does not inhibit the binding of the other to human IgE, thus recognizing different regions of D$\epsilon$1 domain from each other.

Thus, any one of the monoclonal antibodies according to the present invention binds to human IgE at a region different from regions for the other antibodies without receiving any interference from the bindings of the other antibodies to human IgE.

All of the monoclonal antibodies according to the present invention strongly bind to intact human IgE but not to human IgE which have been denatured by guanidine hydrochloride or 2-mercaptoethanol.

All of the monoclonal antibodies according to the present invention are classified into mouse immunoglobulin G.

Since the monoclonal antibodies according to the present invention independently bind to human IgE with different affinities, a mixture of the antibodies with controlled reactivity to human IgE can be obtained by appropriately mixing two or more of the antibodies. For example, in sandwich immunoassay using monoclonal antibody HE-69B immobilized, IgE of wide range concentrations can be determined with controlled calibration curve when a mixture of the monoclonal antibodies HE-22A, HE-35A, and HE-39E (2 to 7:1:5 to 20, as protein concentration), which have equal specific activity of label per antibody, was employed as a labelled antibody. Thus, a monoclonal antibody mixture which has a desired reactivity with human IgE can be obtained by mixing at least two different antibodies selected from the group consisting of HE-22A, HE-35A, and HE-39E of the present invention.

Also provided by this invention are the monoclonal antibodies and the mixture thereof which have been labelled with radioisotopes such as $^{125}$I, enzymes such as horse radish peroxidase, or other known label compounds such as biotin and avidin.

The present invention further provides hybridoma cell lines producing the monoclonal antibodies described above.

The present invention also provides a method for an immunoassay of human IgE comprising:

immobilizing a monoclonal antibody selected from the group consisting of monoclonal antibodies HE-22A, HE-35A, HE-39E and HE-69B described above;

contacting the immobilized antibody with a sample containing human IgE to bind the immobilized antibody to the human IgE; and binding the human IgE which has been bound to the immobilized antibody to a labelled antibody which is selected from said group and is different from that immobilized.

Any one of the monoclonal antibodies according to the present invention recognizes a site different form the others and does not inhibit the binding of the others to IgE, whereby such a sandwich immunoassay can be effected. As shown in Examples described below, any one of the antibodies can be used for immobilization and any one of the other three can be used as a labelled antibody.

Furthermore, the present invention provides an immunoassay of human IgE comprising:

immobilizing a monoclonal antibody HE-69B described above;

contacting the immobilized antibody with a sample containing human IgE to bind the immobilized antibody to the human IgE; and binding the labelled mixture of monoclonal antibodies as mentioned above to the human IgE which has been bound to the immobilized antibody. This method is preferable since IgE of wide range concentrations can be determined with a linear calibration curve.

The present invention still further provides an immunoassay of an antigen-specific human IgE antibody comprising:

contacting an immobilized antigen with a sample containing human IgE;

binding a human IgE antibody specific to the antigen contained in the sample to the immobilized antigen; and binding a labelled monoclonal antibody to the human IgE antibody which has been bound to the immobilized antigen.

For example, when an acarian antigen is used as an immobilized antigen, acarian-antigen specific IgE in a sample such as human blood can exclusively be determined.

A concentration of IgE in the sample assayed can be calculated by using a calibration curve made by using IgE solutions of fixed different concentrations.

EXAMPLE 1

(1) Immunization

Human IgE (200 µg) in Freund's complete adjuvant was administered intraperitoneally to each of 3 female BALB/c mice of 8 weeks old and after 3 weeks further 20 µg of human IgE in a form of alum precipitation suspension was intraperitoneally administered to each mouse for successive 3 days.

(2) Cell fusion

On the next day of the final immunization, spleens were removed from 3 mice and a cell suspension thereof was prepared using RPMI medium. The Spleen cells ($3\times10^8$) thus obtained and NS-1 myeloma cells ($9\times10^7$) were mixed and centrifuged to obtain a pellet, to which 1 ml of 50% polyethylene glycol (average molecular weight of 4000) was added slowly while stirring, followed by stirring for another 1 minute, 1 ml of RPMI medium was added over 1 minute, and another 1 ml was added, then further 7 ml was added over 3 minutes. After centrifugation, the pellet was suspended in 60 ml of RPMI medium containing 15% fetal bovine serum (complete RPMI medium), and then 0.1 ml of the suspension was placed to each well of total 6 plates of 96-well microplates, which were incubated in the presence of 7% $CO_2$ at 37° C. After 24 hours, 0.1 ml of complete RPMI medium containing 100 μM hypoxanthine, 0.4 μM aminopterin and 16 μM thymidine (HAT medium) was added. On days 2, 3, 5, and 8 after initiation of the incubation, 0.1 ml of the supernatant of each culture was discarded and 0.1 ml of HAT medium was added. On days 11 and 14, 0.1 ml of the supernatant was discarded and 0.1 ml of complete RPMI medium containing 100 μM hypoxanthine and 16 μM of thymidine (HT medium) was added. In 460 of total 506 wells, hybridoma colonies were developed.

(3) Screening of hybridoma

Hybridomas in the wells were incubated in complete RPMI medium and the production of specific antibodies in the supernatant of the culture was examined as follows.

A solution (50 μl) of 10 μg/ml human IgE (used in immunization: IgE. λ) dissolved in 0.01M phosphate buffered saline (pH 7.4) was added to each well of polystyrene microtiterplates and allowed to stand at 37° C. for 1 hour and then 100 μl of 0.01M phosphate buffered saline (pH 7.4) containing 10% fetal bovine serum was added and allowed to stand at 37° C. for 20 minutes for the blocking. The plates were washed with 0.01M phosphate buffered saline (pH 7.4) containing 0.05% Tween 20 to complete human IgE-immobilized wells. The human IgE-immobilized wells each received 50 μl of the culture supernatant and were incubated at 37° C. for 1 hour. After washing in the same way as described above, 50 μl of rabbit anti-mouse IgG (H+L) antibody labelled with horse radish peroxidase was added as a second antibody and incubated at 37° C. for 1 hour. After washing as described above, 50 μl of 50 mM citrate buffer (pH 4.5) containing 1.1% hydrogen peroxide and 150 μg/ml azinobis (3-ethylbenzothiazolin-6-sulphonic acid) (ABTS) was added and color was developed at 25° C. for 5 minutes. The reaction was terminated by adding 50 μl of 2 mM sodium azide, and absorbance at 450 nm was determined by using a spectrophotometer for microplates, and total 145 wells of hybridomas exhibiting absorbance of 0.5 or higher were selected.

Of the hybridomas producing antibodies against the immunogen human IgE, the reactivity to human IgE (IgE. κ) different from the immunogen and to human IgG was examined by ELISA as described above. Then, 40 wells of hybridomas producing antibodies which reacted strongly with two human IgEs but not with human IgG were selected. The selected hybridomas were cloned by the limiting dilution method and the supernatant of the hybridoma clones developed was tested for the reactivity of the antibodies to human IgE. λ, human IgE. κ, human IgA, human IgG, human IgM, and human immunoglobulins λ chain and κ chain by ELISA.

Consequently, 40 clones of the hybridomas which produce monoclonal antibodies specifically reactive to human IgE were obtained.

Among these hybridomas, those which produce monoclonal antibodies having the characteristics mentioned above and suitable for the human IgE immunoassay of the present invention as shown in Experiments described below were selected. Thus, hybridoma HE-39E Shionogi (FERM P-11381), HE-22A Shionogi (FERM P-11382), HE-69B Shionogi (FERM P-11383), and HE-35A Shionogi (FERM P-11384) producing monoclonal antibodies HE-39E, HE-22A, HE-69B and HE- 35A, respectively, were obtained.

(4) Preparation of monoclonal antibodies (a) In vitro incubation

Hybridomas were incubated in complete RPMI medium until growth limit ($1\times10^6$ cells/ml) and the supernatant of the culture was collected.

(b) In vivo incubation

Hybridoma cells ($5\times10^6$) were transplanted intraperitoneally to BALB/c mice previously treated intraperitoneally with 0.5 ml of pristane. After about 3 weeks, the mice were observed to ensure the abdominal swelling and then ascitic fluid was collected.

(5) Purification of monoclonal antibodies

Ascitic fluid obtained above was precipitated with 18% sodium sulfate solution and the precipitation formed was dissolved in 0.01M borate buffered saline (pH 8.0) and then subjected to dialysis against the same solution. The monoclonal antibodies (20 mg) obtained by salt precipitation was dissolved in 2 ml of 0.01M borate buffered saline (pH 8.0) and adsorbed to protein A-Sepharose column (Pharmacia AB, 1.5×5 cm). The column was eluted with about 50 ml of 0.01M borate buffered saline (pH 8.0) to eliminate contaminants, and then with about 100 ml of 0.01M citrate buffered saline (pH 4.0) to yield purified monoclonal antibodies.

Experiment 1

Reactivity to human immunoglobulins

Each 50 μl of solutions (10 μg/ml) of two human IgEs, IgE. λ (immunogen) and IgE. κ (Serotech), human IgA (Cappel), human IgM (Miles), human IgG (Miles) and human immunoglobulins L chain type λ and L chain type κ dissolved in 0.01M phosphate buffered saline (pH 7.4) was added to each well of polystyrene microtiterplates, and allowed to stand at 37° C. for 1 hour, and then 100 μl of 0.01M phosphate buffered saline (pH 7.4) containing 10% fetal bovine serum was added and the wells were blocked at 37° C. for 20 minutes. The wells were washed with 0.01M phosphate buffered saline(pH 7.4) containing 0.05% Tween 20, and wells on which each human immunoglobulin was immobilized were obtained. Then, each 50 μl of solutions (10 μg/ml) of purified monoclonal antibodies HE-22A, HE-35A, HE-39E, and HE-69B dissolved in 0.01M phosphate buffered saline (pH 7.4) containing 10% fetal bovine serum was added and allowed to react for 1 hour at 37° C. After washing in the same way as described above, color development was conducted as described in Example 1-(3) to determine the absorbance.

As shown in Table 1, each of monoclonal antibodies HE-22A, HE-35A, HE-39E, and HE-69B reacted with two human IgEs but not with the other human immunoglobulins.

Experiment 2

Iodine ($^{125}$I)-labelling of monoclonal antibodies

A solution (50 μl) of 40 μg/ml of 1, 3, 4, 6-tetrachloro-3α, 6α-diphenylglycoluryl (IODO-GEN, Pierce Chemical) in dichloromethane was placed in a glass tube, which was then allowed to stand for dryness. Each 25 μl of 2 mg/ml solution of monoclonal antibody HE-22A, HE-35A, HE-39E, or HE-69B dissolved in 0.1M phosphate buffer solution (pH 7.4) was added to each glass tube and then 0.5 mCi/5 μl radioactive sodium iodide ($Na^{125}I$) was added and agitated gently at room temperature for 15 minutes. The reaction solution obtained was applied to Sephadex G-25 column (Pharmacia, 1.6×18 cm) and eluted with phosphate buffered saline. Earlier fractions were collected to obtain $^{125}$I-labelled monoclonal antibodies HE-22A, HE-35A, HE-39E, and HE-69B.

Experiment 3

Horse radish peroxidase (HRP)-labelling of monoclonal antibodies

HRP (5 mg) was dissolved in 2 ml of 0.01M acetate buffer solution and 2 mg of sodium methaperiodate dissolved in 0.2 ml of the same buffer was added and allowed to react at 25° C. for 20 minutes. The reaction solution obtained was applied to Sephadex G-25 column (1.6×18 cm) and eluted with 0.001M acetate buffer solution (pH 4.5). According to the absorbance at 413 nm, initial fractions were collected to yield 1.4 mg of activated HRP, to which 2 mg of HE-22A, HE-35A, HE-39E or HE-69B dissolved in 1.2 ml of 0.1M carbonate buffered saline was added and allowed to react at 25° C. for 2 hours. An aqueous solution (0.1 ml) of 0.2 mg of sodium borohydrite was added and allowed to react at 4° C. for 2 hours. The resulting mixture was applied to Sephadex G-25 column (1.6×18 cm), which was eluted with 0.01M phosphate buffered saline (pH 7.4). Initial fractions (4 ml) were collected and applied to Sephacryl S-200 column (Pharmacia, 1.6×70 cm), which was then eluted with 0.0M phosphate buffered saline (pH 7.4). Initial fractions were collected to yield each of HRP-labelled monoclonal antibodies HE-22A, HE-35A, HE-39E, and HE-69B.

Experiment 4

Reactivity with heat-treated IgE

A solution (1.5 ml) of 10 μg/ml of human IgE in 0.01M phosphate buffered saline (pH 7.4) containing 10% fetal bovine serum was heated at 56° C. for 2 hours.

In the same way as in Experiment 1, prepared were plates having wells on which monoclonal antibodies HE-22A, HE-35A, HE- 39E, and HE-69B each was immobilized. Then, 50 μl of 500, 167, 56, 19 or 2.1 ng/ml solution of heat-treated human IgE was added to each well and allowed to react at 37° C. for 1 hour. As a control, untreated human IgE of the same concentrations was used. After washing, 50 μl of 10 μg/ml solution of HRP-labelled monoclonal antibody ID-15F (reactive with an idiotype part of the antigen human IgE) was added and allowed to react at 37° C. for 1 hour. After washing, color development was effected in the same way as in Example 1-(3) to determine the absorbance.

As shown in FIG. 1, monoclonal antibodies HE-22A and HE-69B well reacted with heat-treated human IgE, while HE-35A exhibited significantly reduced reactivity with heat-treated human IgE. It is known that such heat treatment causes the modification of the structure of IgE at Dε2region. Thus, HE-35A recognizes the heat-sensitive Dε2 region.

Experiment 5

Reactivity against IgE treated with endoglycosidase F

Endoglycosidase F is an enzyme which cleaves sugar chains of glycoproteins.

A solution (0.1 ml) of 5 mg/ml of human IgE in physiological saline was admixed with70.12 ml of 8.3 U/ml of endoglycosidase F in 0.1M phosphate buffer solution (pH 6.1) containing 50 mmol/L sodium ethylenediaminetetraacetic acid, 0.05% sodium azide, 0.5% sodium dodecylsulfate, and 0.05% Tween 20 and allowed to react at 37° C. for 20 hours to give endoglycosidase F-treated human IgE.

In the same way as in Example 1-(3), endoglycosidase-treated human IgE was immobilized on wells of plates. As a control, intact human IgE-immobilized plates were prepared. Then, 50 μl of a solution of HRP-labelled monoclonal antibody HE-22A, HE-35A, HE-39E, or HE-69B in 0.01M phosphate buffer solution (pH 7.4) containing 10% fetal bovine serum was added to each well and allowed to react at 37° C. for 1 hour. After washing, color development was carried out in the same way as that used in Example 1-(3) to determine the absorbance.

As shown in Table 2, monoclonal antibodies HE-35A, HE-39E, and HE-69B reacted with endoglycosidase F-treated human IgE, while HE-22A did not. Therefore, HE-22A recognizes the structure closely related with sugar chains of IgE.

Experiment 6

Reactivity of monoclonal antibodies in inhibition test

Human IgE-immobilized plates were prepared in the same way as that in Example 1-(3). Then, 50 μl of 10 μg/ml solution of HRP labelled monoclonal antibody HE-22A, HE-35A, HE-39E, or HE-69B and 50 μl solution of unlabelled monoclonal antibodies HE-22A, HE- 35A, HE-39E, HE-69B, anti-Dε1 antibody, or anti-Cε4 antibody (2000, 500, 125, 31.2, 7.8, or 0 μg/ml) was added to each well and allowed to react with 37° C. for 1 hour. After washing, color development was carried out in the same way as that used in Example 1-(3) to determine the absorbance.

As shown in Table 3, each of HE-22A, HE-35A, HE-39E, and HE- 69B inhibited the same antibody on the reaction with human IgE, whereas each of them did not inhibit the other antibodies on the reaction. HE-39E and HE-69B inhibited monoclonal anti-Dε1 antibody on the reaction. No antibody was inhibited by monoclonal anti-Cε4 antibody.

Experiment 7

Reactivity with denatured IgE

A solution (0.2 ml) of 5 mg/ml human IgE in physiological saline and an aqueous solution (0.2 ml) containing 6M/L guanidine hydrochloride and 4% 2-mercaptoethanol was admixed and allowed to react at 60° C. 2 hours to yield denatured human IgE.

In the same way as that used in Example 1-(3), monoclonal antibodies HE-22A, HE-35A, HE-39E, and HE-69B each was immobilized on plates. After washing, 50 μl of 1 μg/ml solution of denatured human IgE obtained above in 0.01M phosphate buffered saline containing 10% fetal bovine serum was added to each well and allowed to react at 37° C. for 1 hour. As a control, 50 μl of 1 μg/ml solution of intact human IgE was added and allowed to react at 37° C. for 1 hour. After washing, 50 μl of 10 μg/ml solution of HRP-labelled monoclonal antibody HE-22A, HE-35A, HE-39E, or HE-69B in 0.01M phosphate buffered saline containing 10% fetal bovine serum was added and allowed to react at 37° C. for 1 hour. After washing, color was developed in the same way as in Example 1-(3) to determine the absorbance.

As shown in Table 4, monoclonal antibodies HE-22A, HE-35A, HE-39E, and HE-69B reacted with intact IgE but not with denatured IgE.

Experiment 8

Sandwich assay of IgE

In the same way as that used in Example 1-(3), monoclonal antibodies HE-22A, HE-35A, HE-39E, and HE-69B each was immobilized on plates. After washing, each 50 μl of 10,000, 2,000, 400, 80, 16 and 0 IU/ml solutions of human IgE in 0.01M phosphate buffered saline (pH 7.4) containing 10% fetal bovine serum was added and allowed to react at 37° C. for 1 hour. After washing in the same way as that used in Experiment 5, reaction with HRP-labelled monoclonal antibody HE-22A, HE-35A, HE-39E, or HE-69B was conducted, followed by color development and determination of the absorbance.

As shown in FIG. 2, among the combinations of any one of the immobilized monoclonal antibodies with any one of the HRP-labelled monoclonal antibodies, the combinations of heterogeneous antibodies served as assay systems of high reactivity with human IgE, while the combinations of homogeneous antibody resulted in assay systems of low reactivity.

Experiment 9

Affinity constant to Human IgE

Mite (dermatophagoides pteronisinus; DP)-specific IgE-positive human sera were mixed to obtain 50 ml of serum pool. This pooled serum (200 μl) was placed in a test tube(SHIONOGI TUBE™) SHIONOGI TUBE™ is a polystyrene test tube 1 cm×7 cm, with a polyethylene cap and 1 bead of DP antigen-conjugated beads (MITE-SPECIFIC IgG TEST: SHIONOGI™) MITE-SPECIFIC IgG TEST: SHIONOGI™ is an immunodiagnostic test for mite (D. pteronisinus)-specific IgG was added and allowed to react at 25° C. for 3 hours while shaking. After washing with 0.01M phosphate buffer (pH 7.4) containing 0.05% Tween 20, 200 μl of 10, 5, 2.5, 1.25, 0.625, 0.313, or 0.156 μCi/ml solution of $^{125}$I-labelled monoclonal antibody HE-22A, HE-35A, HE-39E or HE-69B in 0.01M phosphate buffer (pH 7.4) containing 10% fetal bovine serum was added and allowed to react at 25° C. for 16 hours while shaking. After washing, radioactivity in each tube was counted by a γ-counter.

As shown in Table 5, HE-35A, HE-69B, HE-22A, and HE-39E exhibited higher affinity with DP-specific IgE antibodies in this order, and HE-35A, HE-69B, HE-22A, and HE-39E could bind to a larger number of sites (epitope density) in this order.

Experiment 10

Human IgE assay

A solution (200 ml) of 40 μg/ml of monoclonal antibody HE- 69B in 0.01M phosphate buffered saline (pH 7.4) was applied to 100 particles of polystyrene beads (Immunochemical) and allowed to stand at 37° C. for 20 hours. After discarding the solution, the beads were washed with 0.01M phosphate buffered saline (pH 7.4) and admixed with 200 ml of 0.01M phosphate buffer solution (pH 7.4) containing 0.1% bovine serum albumine and allowed to stand at 37° C. for 3 hours. The beads were washed with 0.01M phosphate buffered saline (pH 7.4) containing 0.05% Tween 20 to obtain monoclonal antibody HE-69B-conjugated beads.

Solutions of 5,000, 1,000, 200, 40, 8, 1.6 and 0 IU/ml of human IgE in 0.01M phosphate buffered saline containing 10% fetal bovine serum were prepared and 50 μl of each solution was placed in each tube. To each tube was added 100 μl of 3.7 μCi/ml solution of $^{125}$I- labelled monoclonal antibodies HE-22A, HE-35A or HE-39E or 100 μl of 3.7 μCi/ml solution of the mixture of HE-22A, HE-35A, and HE-39E. One particle of monoclonal antibody HE-69B-conjugated beads was added to each tube and allowed to react at 25° C. for 3 hours. After washing, radioactivity in each tube was counted by a γ-counter.

Figure 3:
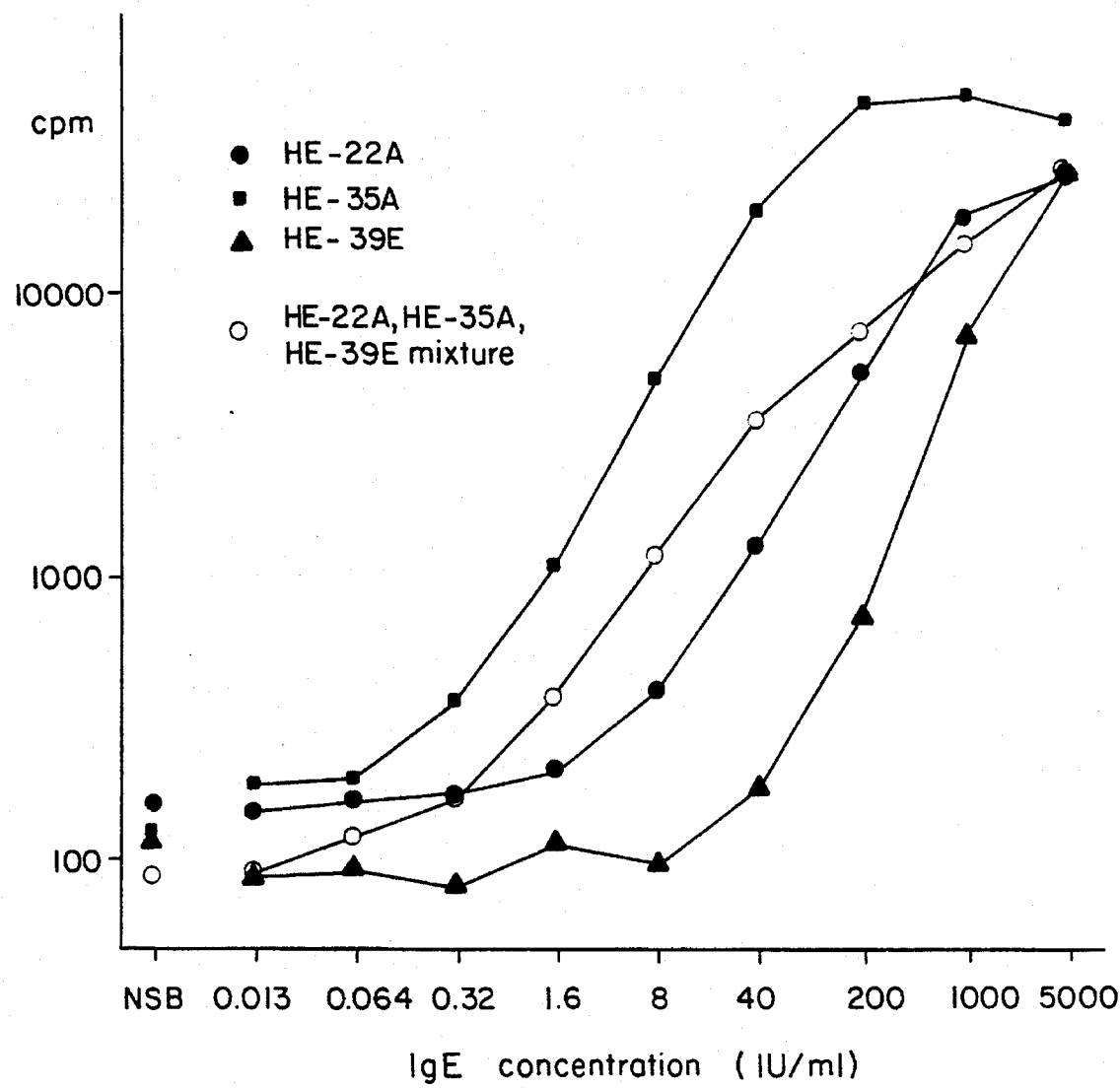
FIG. 3 shows the sensitivity curves of each of 3 monoclonal antibodies (HE-22A, HE-35A and HE-39E) and of the mixture of these three antibodies in sandwich RIA system using the monoclonal antibody HE-69B-immobilized beads.

As indicated in FIG. 3, HE-35A, HE-22A, and HE-39E gave the sensitivity curves for human IgE within human IgE concentration ranges of 0.32 to 200 IU/ml (625-fold), 1.6 to 1,000 IU/ml (625-fold) and 40 to 5,000 IU/ml (125-fold), respectively. On the other hand, the mixture of $^{125}$I-labelled monoclonal antibodies HE-22A, HE-35A, and HE-39E of certain protein ratio (3:1:6), all of which have equal specific radioactivity, gave the sensitivity curve covering wide range of concentrations of human IgE from 0.32 to 5000 IU/ml (15,625-fold).

TABLE 1

Reactivity of monoclonal antibody with human immunoglobulin in ELISA method

| Clone No. | IgE/λ | IgE/κ | IgA | IgM | IgG | λ | κ |
|---|---|---|---|---|---|---|---|
| HE-22A | ++ | ++ | − | − | − | − | − |
| HE-35A | ++ | ++ | − | − | − | − | − |
| HE-39E | ++ | ++ | − | − | − | − | − |
| HE-69B | ++ | ++ | − | − | − | − | − |

++: Highly positive
+: Positive
−: Negative

TABLE 2

Reactivity of monoclonal antibody with IgE treated with endoglycosidase F

| Antigen IgE | HE-22A | HE-35A | HE-39E | HE-69B |
|---|---|---|---|---|
| (A) IgE | 516 | 214 | 776 | 1031 |
| (B) IgE treated with endoglycosidase F | 12 | 188 | 1051 | 965 |
| (B)/(A) % | 2 | 88 | 135 | 94 |

Absorbance A490 × 1000

TABLE 3

Specificity of reactivity of monoclonal antibody in inhibition test

| Labelled antibody | Immobilized antibody | | | |
|---|---|---|---|---|
| | HE-22A | HE-35A | HE-39E | HE-69B |
| HE-22A | ++ | − | − | − |
| HE-35A | − | ++ | − | − |
| HE-39E | − | − | ++ | − |
| HE-69B | − | − | − | ++ |

++: Highly positive
+: Positive
−: Negative

TABLE 4

Reactivity of monoclonal antibody with denatured IgE in sandwich ELISA system

| Labelled antibody | Immobilized antibody | | | | | | | |
|---|---|---|---|---|---|---|---|---|
| | Intact IgE | | | | Denatured IgE | | | |
| | HE-22A | HE-35A | HE-39E | HE-69B | HE-22A | HE-35A | HE-39E | HE-69B |
| HE-22A | − | ++ | ++ | ++ | − | − | − | − |
| HE-35A | ++ | + | ++ | ++ | − | − | − | − |
| HE-39E | ++ | ++ | − | ++ | − | − | − | − |
| HE-69B | ++ | ++ | ++ | + | − | − | − | − |

++: Highly positive
+: Positive
−: Negative

TABLE 5

Affinity constant of monoclonal antibody for mice allergen-specific human IgE antibody

| Anti IgE | Epitope density (mol/l) | Affinity constant (l/mol) |
|---|---|---|
| HE-22A | $6.4 \times 10^{-10}$ | $1.3 \times 10^8$ |
| HE-35A | $1.5 \times 10^{-9}$ | $1.6 \times 10^9$ |
| HE-39E | $2.6 \times 10^{-10}$ | $1.2 \times 10^8$ |
| HE-69B | $1.3 \times 10^{-9}$ | $1.2 \times 10^9$ |

What we claim is:

1. A composition comprising a mixture of at least three of the monoclonal antibodies selected from the group consisting of monoclonal antibodies secreted from the hybridomas deposited as FERM BP-3342, FERM BP-3343, and FERM BP-3345.

* * * * *